United States Patent [19]

Chang et al.

[11] Patent Number: 4,927,769

[45] Date of Patent: May 22, 1990

[54] METHOD FOR ENHANCEMENT OF CHEMILUMINESCENCE

[75] Inventors: Steve C. S. Chang, Franklin; Thomas E. Miller, Norwood, both of Mass.

[73] Assignee: Ciba Corning Diagnostics Corp., Medfield, Mass.

[21] Appl. No.: 71,660

[22] Filed: Jul. 8, 1987

[51] Int. Cl.$^5$ .................. G01N 33/543; G01N 21/00; G01N 33/531; G01N 33/532

[52] U.S. Cl. ................... 436/518; 252/700; 436/164; 436/543; 436/544; 436/805; 436/826; 530/802

[58] Field of Search ............... 252/700; 435/8; 436/546, 800, 805, 172, 826, 518, 544, 543, 164; 530/802; 546/103

[56] References Cited

U.S. PATENT DOCUMENTS

| | | | |
|---|---|---|---|
| 3,714,054 | 1/1973 | Cline ................................. | 252/700 |
| 4,462,931 | 7/1984 | Cohen et al. ....................... | 252/700 |
| 4,745,181 | 5/1988 | Law et al. .......................... | 530/387 |

FOREIGN PATENT DOCUMENTS 0175889  4/1986  European Pat. Off. ............ 252/700

OTHER PUBLICATIONS

McCopra, Accounts of Chemical Research 9(6), 201-208 (1976).
Weeks et al., Clinical Chemistry 29(8), 1474-1479 (1983).
Hackh's Chemical dictionary, 3rd Edition, McGraw Hill Book Co., NY, 1944, pp. 43, 818, 817.

*Primary Examiner*—Esther M. Kepplinger
*Assistant Examiner*—Florina B. Hoffer
*Attorney, Agent, or Firm*—Nicholas I. Slepchuk; William G. Gosz

[57] ABSTRACT

A method for enhancing the chemiluminescent signal of an acridinium ester in a chemiluminescent reaction which comprises oxidizing the acridinium ester in the presence of an enhancer selected from the group consisting of: (a) a cationic surfactant; (b) a nonionic surfactant; and (c) a sulfated primary alcohol.

13 Claims, No Drawings

METHOD FOR ENHANCEMENT OF CHEMILUMINESCENCE

FIELD OF THE INVENTION

This invention relates to a method for the enhancement of chemiluminescence. In particular, this invention relates to a method for the enhancement of the chemiluminescence of acridinium esters. This invention further relates to an enhanced chemiluminesctn immunoassay.

BACKGROUND OF THE INVENTION

Immunoassay has become the method of choice for the quantitation of a large variety of biologically important molecules. Many of the immunoassays utilize a radioactive label. However, because of the inherent problems with using radioactive labels, a number of chemiluminescent and bioluminescent compounds have been used in innumoassay systems as labels on either antigen or antibody. Due to the exothermic nature of chemiluminescent reactions, their quantum yield in general, is very low (<1%) compared to the bioluminescent systems. Ways to enhance the quantum yield of the chemiluminescent reactions are, therefore, desirable.

European Patent No. 0087959 describes an assay utilizing a 6-hydroxy-benzothiazole to enhance the chemiluminescent sensitivity of 2, 3-dihydro-1, 4-phthalazinedione.

U.K. Patent Application GB 2162946A describes the use of certain aromatic amines to enhance the sensitivity of the luminescent reaction of the peroxidase-catalysed oxidation of 2, 3-dihydro-1, 4-phthalazinedione.

In Whitehead et al., "Enhanced Luminescence Procedure for Sensitive Determination of Peroxidase-Labelled Conjugates in Immunoassays," Nature 305, pp 158-159 (1983), the authors describe the use of luciferin in a horseradish-mediated luminol chemiluminescent reaction to increase the chemiluminescent signal.

Prior to the present invention, no procedure was known for enhancing the chemiluminescent signal generated by acridinium esters.

Accordingly it is an object of the present invention to provide a method for the enhancement of the chemiluminescence of acridinium esters.

It is also an object of the invention to provide an enhanced chemiluminescent immunoassay.

DESCRIPTION OF THE INVENTION

This invention relates to a method for enhancing the chemiluminescent signal of an acridinium ester in a chemiluminescent reaction which comprises oxidizing the acridinium ester in the presence of an effective amount of an enhancer selected from the group consisting of (a) a cationic surfactant; (b) a nonionic surfactant; and (c) a sulfated primary alcohol.

The enhancers useful in the process of this invention should be soluble in the reagents and under the conditions necessary for the chemiluminescent reaction. "Soluble" for the purposes of this invention means the lack of a percipitate.

Cationic surfactants are discussed in, among other places, *Surfactants and Interfacial Phenomena*, by Milton J. Rosen (hereinafter referred to as Rosen), John Wiley and Sons, N.Y., 1978, pages 13-17.

Typical cationic surfactants include long-chain amines and their salts, such as primary amines derived from animal and vegetable fatty acids, tall oil, synthetic $C_{12}$–$C_{18}$ primary, secondary or tertiary amines; diamines and polyamines and their salts, such as N-alkyltrimethylenediamine salts and N-alkylimidazolines; quaternary ammonium salts, such as N-alkytrimethylammonium choorides or N, N-dialkyldimethylammonium chlorides; polyoxyethylenated long-chain amines of formula $RN[(CH_2CH_2O)_xH]_2$; quaternized polyoxyethylenated long-chain amines of formula $RN(CH_3)[(C_2H_4O)_xH]_2{}^+Cl^-$; and amine oxides such as N-alkyldimethylamine oxides.

Prefered cationic surfactants are long chain amines, polyoxyethylenated long chain amines, and quaternary amines. Particularly preferred are quaternary amines of the formula:

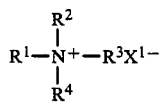

wherein $R^1$ is $C_8$–$C_{20}$ alkyl or akenyl; $R^2$, $R^3$ and $R^4$ are $C_1$–$C_4$ alkyl or alkenyl; and $X^1$ is halide. More preferably $R^1$ is $C_6$–$C_{20}$. Especially preferred are quaternary amines wherein $R^1$ is $C_{14}$–$C_{16}$; $R^2$, $R^3$ and $R^4$ are methyl or ethyl; and $X^1$ is chlorine or bromine. Useful quaternary amines include hexadecyltrimethylammonium chloride, dodecyltrimethylammonium chloride, cetyltrimethylammonium bromide, cocotrimethylammonium chloride, tallowtrimethylammonium chloride, soyatrimethylammonium chloride, and the like.

Commercially available cationic surfactants useful in the method of this invention include ARMEEN OD, ETHOMEEN S-20, BRETOL and ARQUAD.

Nonionic surfactants are discussed in, among other places, Rosen at pages 17-22, the pertinent portions of which are herein incorporated by reference. Preferred nonionic surfactants include polyoxyethylenated nonionic surfactants such as polyoxyethylenated alkylphenols, polyoxyethylenated straight-chain alcohols, polyoxyethylenated sorbitol esters and the like, and alkanolamine-fatty acid condensates. Commercially available non-ionic surfactants useful in the method of this invention include TRITON X-100, TWEEN 80, BRIJ-35, SOLULAN 16 and oleic acid diethanolamide.

Sulfated primary alcohols are discussed in, among other places, Rosen at page 11. Sulfated linear primary alcohols include the sodium and magnesium salts of the $C_{12}$, oleyl and $C_{16}$–$C_{20}$ primary alcohols. Preferred sulfated primary alcohols (also known as alkyl sulfates) include sodium dodecylsulfate (also known as SDS and as sodium lauryl sulfate), magnesium dodecylsulfate and sodium tridecylsulfate.

Acridinium esters useful in the method of this invention can be depicted by the formula:

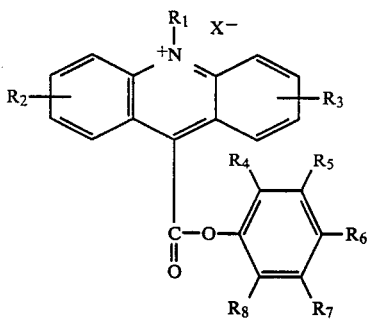

where $R_1$ is alkyl, alkenyl, alkynyl, or aryl; $R_2$, $R_3$, $R_5$, or $R_7$ are hydrogen, amino, carboxyl, hydroxyl, alkoxyl, nitro, or halide; $R_4$ or $R_8$ are hydrogen, alkyl, alkenyl, alkynyl, aryl, akoxyl, amino, amido, sulfonamido, or sulfide; $R_6$ represents the following substituent:

$R_6 = -R_9 - R_{10}$ where $R_9$ is not required but optionally can be alkyl, aryl, or aralkyl, and $R_{10}$ is selected from the following:

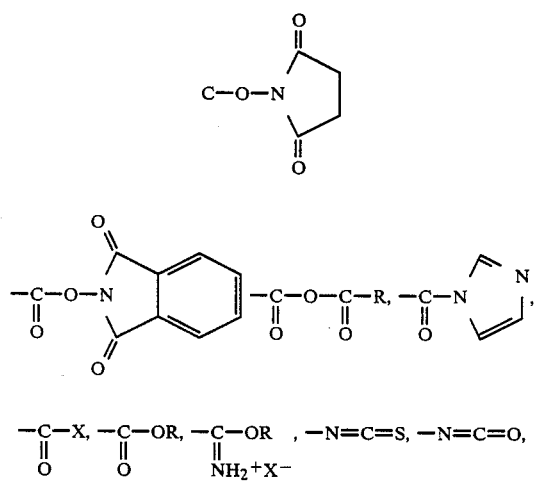

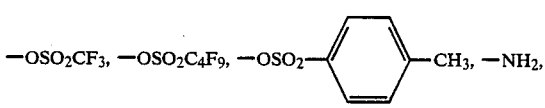

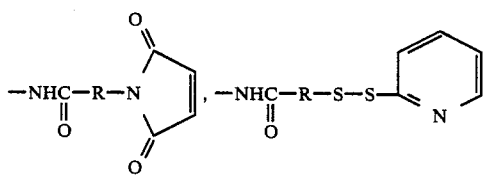

X is $CH_3SO_4^-$, $OSO_2F^-$, halide, $OSO_2CF_3^-$, $OSO_2C_4F_9^-$,

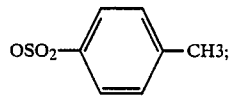

and R is alkyl, aryl, aralkyl; and finally $R_5$, $R_6$, and $R_7$ substituent positions on the phenoxy ring are interchangeable.

Preferably, $R_4$ and $R_8$ are alkyl, alkenyl, alkynyl, aryl, alkoxyl, amino, amido, sulfonamido, or sulfide. More preferably, $R_1$ is methyl, $R_2$, $R_3$, $R_5$, and $R_7$ are hydrogen; $R_4$ and $R_8$ are methyl, $R_{10}$ is an N-succinimidyloxycarbonyl group attached directly to the para-position of the phenoxy ring, and X is $CH_3SO_4$.

Useful acridinium esters are described in copending U.S. Application Ser. No. 915,527, filed Oct. 6, 1986, herein incorporated by reference.

The acridinium ester can be oxidized by any oxidant which reacts with the ester to cause excitation of the ester so that the ester emits light in a chemiluminescent reaction. A preferred oxidant is hydrogen peroxide in dilute alkali.

For the purposes of this invention "enhancing" means that the total light emission of the chemiluminescent reaction and/or the signal to background noise ratio of the chemiluminescent reaction is greater than that achieved by the acridinium ester in the absence of the enhancer useful in the present invention.

The effective amount of enhancer necessary to enhance the chemiluminescent signal of the acridinium ester in a chemiluminescent reaction will vary depending on the enhancer chosen and should be determined empirically. As a general rule, an effective amount of enhancer in a chemiluminescent reaction mixture is greater than 0.005% by weight, preferably greater than 0.01% by weight.

Light emission from the chemiluminescent reaction of the present invention will depend primarily on the choice of acridinium ester, oxidant and enhancer. However, secondary reaction conditions such as temperature, pH, reagent concentration, mixing speed and method of light measurement will also affect the amount of light emitted. It is preferable that the secondary reaction conditions be adjusted to obtain maximum light emission with the signal to background noise ratio as high as possible.

In the preferred embodiment of the present invention, utilizing a quarternary amine, such as ARQUAD, the chemiluminescent reaction should be conducted at a temperature of from 20° C. to 30° C. and at a pH in the range of 10 to 13. The enhancer is preferably diluted prior to use in the method of this invention. Suitable diluents include water, aqueous acid solutions or aqueous basic solutions. The concentrations of the reagents in the chemiluminescent reaction mixture are kept constant with the exception of the material to be determined. Utilizing the preferred enhancer, i.e. ARQUAD, the following range of final reagent concentrations in a chemiluminescent reaction mixture are preferred for use in the method of this invention:
ARQUAD 0.01% to 0.1% by weight
Oxidant 0.0125% to 0.0625% by weight
Acridinium Ester 1 fmole to 1 pmole The method of this invention can be performed by placing certian of the three essential reagents above in a sample tube, omitting at least one. The chemiluminescent reaction is then triggered by the addition of the missing essential reagent or reagents to the tube. The light emitted can then be quantified using a standard measuring device such as a Model 810 Luminometer (Ciba-Corning Diagnostics Corp., Medfield, MA).

The method of this invention is useful in procedures in which an acridinium ester is used as a chemiluminescent tracer and is particularly useful in immunoassays in which an acridinium ester is used as a chemiluminescent label (see, e.g., Woodhead, et al., "Chemiluminescence Labelled Antibodies and Their Applications in Immunoassays," *Luminescent Assays: Perspectives in Endocrinology and Clinical Chemistry,* pp. 147–155, Raven Press, N.Y., 1982).

The following examples are presented to illustrate the present invention.

EXAMPLE 1

Materials

Monoclonal mouse anti-human thyroid stimulating hormone (h-TSH) is labelled with 2', 6'-dimethyl-4'-(N-succinimidyloxy-carbonyl)phenyl acridine-9-carboxylate by the procedure described in Weeks et al. Clinical Chemistry 29(8), 1474–1479 (1983).

ARQUAD (hexadecyltrimethylammonium chloride) (>99% purity) was obtained from Armak Chemicals, Chicago, Illinois.

Model L950 Luminometer was obtained from Laboratorium Berthold, Wildbad, West Germany.

Resuspension Solution: 0.1% hyrogen peroxide in 0.1N $HNO_3$.

Flashing Solution: 0.3N NaOH.

Buffer: 0.01M Na phosphate, pH 7.4, 0.1% BSA, 0.05% Na azide.

Method

Each 12×75mm sample tube contained 10ul of a solution of the acridinium ester labelled h-TSH in Buffer or contained 10ul of Buffer without the labelled h-TSH. To each tube was then added either a 100ul solution of 0.1N HCl plus a sufficient amount of enhancer (ARQUAD, SDS, or TRITON X-100) to produce the desired final concentrations of enhancer in the reaction solution (see Table 1), or 100ul of 0.1N HCl without enhancer. Each sample tube was placed in the luminometer.

The luminometer then delivered 300ul each of Resuspension Solution and Flashing Solution with an interval of about 1 second between the two injections. The chemiluminescent emission was then measured over time and recorded by the luminometer.

The chemiluminescent emission measured from the samples without the labelled h-TSH was considered noise (or background). The chemiluminescent emission measured from the samples with the labelled h-TSH was considered signal. A signal to noise (S/N) ratio was then calculated for the samples with the labelled h-TSH.

Results

Table 1 shows the S/N ratio of the chemiluminescent reaction over time in the absence and in the presence of ARQUAD, sodium dodecylsulfate (SDS), and TRITON X-100.

TABLE 1

| | EFFECT OF ENHANCER ON S/N RATIO | | | |
|---|---|---|---|---|
| Time (sec) | Control (No enhancer) | ARQUAD[1] | SDS[2] | TRITON X-100[3] |
| 0.5 | 16.7 | 82.0 | 16.3 | 41.5 |
| 1.0 | 22.1 | 73.9 | 29.2 | 48.5 |
| 2.0 | 23.0 | 57.9 | 39.8 | 51.9 |
| 3.0 | 21.4 | 48.0 | 43.6 | 50.4 |
| 4.0 | 19.5 | 41.4 | 45.0 | 47.8 |
| 5.0 | 17.9 | 36.7 | 44.9 | 44.9 |
| 6.0 | 16.6 | 33.1 | 44.3 | 41.9 |

[1]Final concentration was 0.0125% by weight.
[2]Final concentration was 0.5% by weight.
[3]Final concentration was 0.25% by weight.

EXAMPLE 2

Materials

A. Surfactants tested:
1. Sodium dodecylsulfate (SDS)
2. Sodium sulfooleate
3. SULFONATE DE-300 (sodium propylsulfooleate) (obtained from Cities Service Co., Tulsa, OK)
4. TWEEN-80 (sorbitan monooleate polyoxyethylene) (obtained from ICI Americas, Inc., Wilmington, DE)
5. BRIJ-35 (lauryl alcohol ether polyoxyethylene) (obtained from ICI Americas, Inc., Wilmington, DE)
6. SOLULAN 16 (lanolin alcohol ether polyoxyethylene) (obtained from Amerchol Corp., Edison, NJ)
7. Oleic acid diethanolamine
8. ARMEEN OD (oleylamine) (obtained from Armak Chemicals, Chicago, IL)
9. ETHOMEEN S-20 (soya amine polyoxyethylene) (obtained from Armak Chemicals, Chicago, IL)
10. BRETOL (cetyldimethylethylammonium chloride) (obtained from Hexel Chemical, Chatsworth, CA)
11. ARQUAD (hexadecyltrimethylammonium chloride) (obtained from Armak Chemicals, Chicago, IL)

B. First Flashing Solution: 0.1% hydrogen peroxide in 0.1N nitric acid.

C. Second Flashing Solution: 0.2% by weight surfactant in 0.3N NaOH except for ARQUAD which was 0.1% by weight in 0.3N NaOH.

A separate Second Flashing Solution was prepared for each surfactant tested.

D. Model 810 Luminometer was obtained from Ciba Corning Diagnostics Corp., Medfield, MA.

E. Buffer: 0.01M Na phosphate pH 7.4%, 0.1% BSA, 0.05% Na azide.

F. Acridinium ester tracer: 2',6'-dimethyl-4'-(N-succinimidyl-oxycarbonyl) phenylacridine-9-carboxylate.

Method

10ul of Buffer with and without the acridinium ester tracer were placed in 12×75 luminometer tubes for each surfactant to be tested and placed in the Model 810 Luminometer. The luminometer then delivered 0.3ml each of First Flashing Solution and a Second Flashing Solution in sequence with a 1 second span between deliveries of the two solutions. Photon counts were measured for 2 seconds. For each surfactant, Net Count (counts per second) was calculated by subtracting the counts generated in the absence of tracer from the counts generated in the presence of tracer.

A control was run wherein the Second Flashing Solution contained only 0.3N NaOH, i.e. no surfactant.

The results are listed in Table 2.

TABLE 2
Effect of Various Surfactants On The Chemiluminescent Signal Generated by Acridinium Ester

| Surfactant | Net Count (CPS) | CPS/Control CPS |
|---|---|---|
| Control | 86,310 | 1.0 |
| Sodium Sulfooleate | 87,175 | 1.01 |
| SULFONATE DE-300 | 84,065 | 0.97 |
| SDS | 179,085 | 2.07 |
| TWEEN-80 | 154,555 | 1.79 |
| BRIJ-35 | 238,310 | 2.76 |
| SOLULAN 16 | 102,820 | 1.19 |
| Oleic acid diethanolamide | 250,975 | 2.91 |
| ARMEEN OD | 104,595 | 1.21 |
| ETHOMEEN S-20 | 251,080 | 2.91 |
| BRETOL | 99,405 | 1.15 |
| ARQUAD | 499,080 | 5.78 |

What is claimed is:

1. A method for enhancing the chemiluminescent signal of an acridinium ester in a chemiluminescent reaction which comprises oxidizing the acridinium ester in the presence of an effective amount of an enhancer to effect enhanced chemiluminescent signal said enhancer selected from the group consisting of:
   (a) a quarternary amine cationic surfactant of formula:

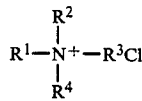

wherein $R^1$ is $C_8$–$C_{20}$ alkyl or alkenyl; and $R^2$, $R^3$ and $R^4$ are $C_1$–$C_4$ alkyl or alkenyl.
   (b) a nonionic surfactant; and
   (c) a sulfated primary alcohol selected from the group consisting of sodium dodecylsulfate, magnesium dodecylsulfate and tridecylsulfate.

2. A method as recited in claim 1 wherein the acridinium ester has the formula:

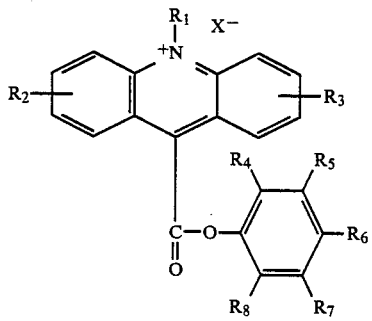

where $R_1$ is alkyl, alkenyl, alkynyl, or aryl; $R_2$, $R_3$, $R_5$, or $R_7$ are hydrogen, amino, carboxyl, hydroxyl, alkoxyl, nitro, or halide; $R_4$ or $R_8$ are hydrogen, alkyl, alkenyl, alkynyl, aryl, alkoxyl, or amino,; $R_6$ represents the following substituent:

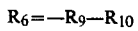

where $R_9$ is omitted or is alkyl, aryl, or aralkyl linking groups, and $R_{10}$ is selected from the group consisting of:

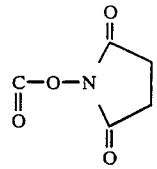

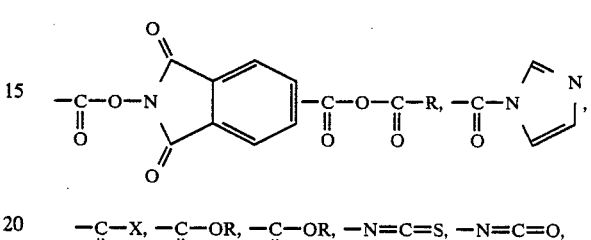

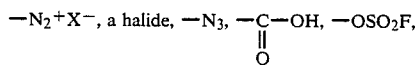

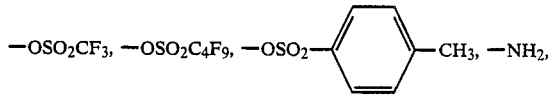

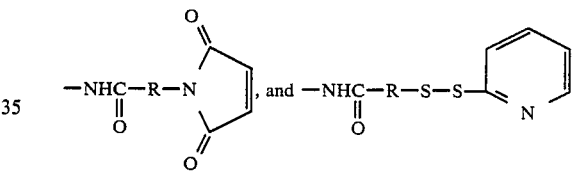

X is $CH_3SO_4$, $OSO_2F$, halide, $OSO_2CF_3$, $OSO_2C_4F_9$, or

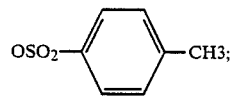

and R is alkyl, aryl, or alralkyl; and finally $R_5$, and $R_7$ substituent positions on the phenoxy ring are interchangeable with the $R_6$ substituent position.

3. A method as recited in claim 2 werein $R_4$ and $R_8$ are alkyl, alkenyl, alkynyl, aryl, alkoxyl, or amino.

4. A method as recited in claim 2 wherein $R_1$ is methyl; $R_2$, $R_3$, $R_5$, and $R_7$ are hydrogen; $R_4$ and $R_8$ are methyl, $R_{10}$ is an N-succinimidyloxycarbonyl group attached directly to the para-position of the phenoxy ring, and X is $CH_3SO_4$.

5. A method as recited in claim 1 wherein the effective amount of enhancer in the chemiluminescent reaction mixture is greater than 0.005% by weight.

6. A method as recited in claim 5 wherein the effective amount of enhancer in the chemiluminescent reaction mixture is greater than 0.01% by weight.

7. A method as recited in claim 1 wherein $R^1$ is $C_{14}$–$C_{16}$ alkyl or alkenyl; $R^2$, $R^3$ and $R^4$ are methyl or ethyl.

8. A method as recited in claim 7 wherein the cationic surfactant is hexadecyltrimethylammonium chloride.

9. A method as recited in claim 1 wherein the enhancer is a nonionic surfactant.

10. A method as recited in claim 9 wherein the nonionic surfactant is a polyoxyethylenated nonionic surfactant.

11. A method as recited in claim 1 wherein the sulfated primary alcohol is sodium dodecylsulfate.

12. In a chemiluscent immunoassasy utilizing an acridinium ester as a label wherein the improvement comprises oxidizing the acridinium ester in the presence of an effective amount of an enhancer selected from the group consisting of:

(a) a quarternary amine cationic surfactant of formula:

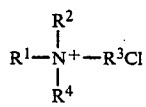

wherein $R^1$ is $C_8$-$C_{20}$ alkyl or alkenyl; and $R^2$, $R^3$ and $R^4$ are $C_1$-$C_4$ alkyl or alkenyl.

13. A chemiluminescent assay as recited in claim 12 wherein $R^1$ is $C_{14}$-$C_{16}$ alkyl or alkenyl; and $R^2$, $R^3$ and $R^4$ are methyl or ethyl.

* * * * *